United States Patent [19]

Smith

[11] 4,368,089
[45] Jan. 11, 1983

[54] METHOD AND APPARATUS FOR MANUFACTURING DENTIFRICE CONTAINING DISPERSED SPECKLES

[75] Inventor: John F. Smith, New Providence, N.J.

[73] Assignee: Colgate-Palmolive Company, New York, N.Y.

[21] Appl. No.: 307,308

[22] Filed: Sep. 30, 1981

[51] Int. Cl.³ .................. B29B 5/00; B29C 19/00
[52] U.S. Cl. .................. 156/243; 156/244.11; 264/75; 264/101; 264/108; 424/49; 425/130
[58] Field of Search .................. 425/130, 131.1, 224; 424/49; 264/73, 75, 101, 108, 171; 156/243, 244.11

[56] References Cited

U.S. PATENT DOCUMENTS

| Re. 27,681 | 6/1973 | Gaddis | 366/153 |
|---|---|---|---|
| Re. 29,634 | 5/1978 | Roberts et al. | 424/57 |
| 2,944,293 | 7/1960 | Taylor | 264/73 |
| 3,499,816 | 3/1970 | Areskoug | 425/130 |
| 3,536,549 | 10/1970 | Goerden et al. | 425/130 |
| 3,681,485 | 8/1972 | Lieberman | 425/130 |
| 3,711,604 | 1/1973 | Colodney et al. | 424/52 |
| 3,740,027 | 6/1973 | Kormos | 366/172 |
| 3,767,791 | 10/1973 | Gordon et al. | 424/49 |
| 3,769,380 | 10/1973 | Wiley | 264/75 |
| 3,803,301 | 4/1974 | Gordon et al. | 424/49 |
| 3,923,941 | 12/1975 | Weaver | 264/73 |
| 3,948,491 | 4/1976 | Karlsson | 366/76 |
| 3,955,942 | 5/1976 | Cordon et al. | 51/295 |
| 4,003,971 | 1/1977 | Mannara | 264/9 |
| 4,089,943 | 5/1978 | Roberts et al. | 424/49 |
| 4,090,262 | 5/1978 | Schneider et al. | 366/155 |
| 4,125,208 | 11/1978 | Bettermann | 366/75 |

OTHER PUBLICATIONS

Chemical Engineering, Handling Viscous Materials—Motionless Mixer for Viscous Polymers, McGraw-Hill, Mar. 19, 1973, pp. 98–104.

Primary Examiner—Donald E. Czaja
Assistant Examiner—W. Thompson
Attorney, Agent, or Firm—Robert L. Stone; Murray M. Grill; Herbert S. Sylvester

[57] ABSTRACT

An improved method for manufacturing a dentifrice containing dispersed speckles therein includes converting a gel or paste dental composition into a plurality of flowing ribbons thereof, directing a stream of speckles onto one such ribbon of dental composition, to which the speckles adhere, bringing together such stream and another stream of such dental compositions so that they adhere together with the deposited speckles sandwiched between them, and controlling relative feed rates of the dental composition and the speckles so that there is produced a dentifrice containing the speckles distributed through it in desired proportion. Also described are apparatuses for carrying out the process.

17 Claims, 2 Drawing Figures

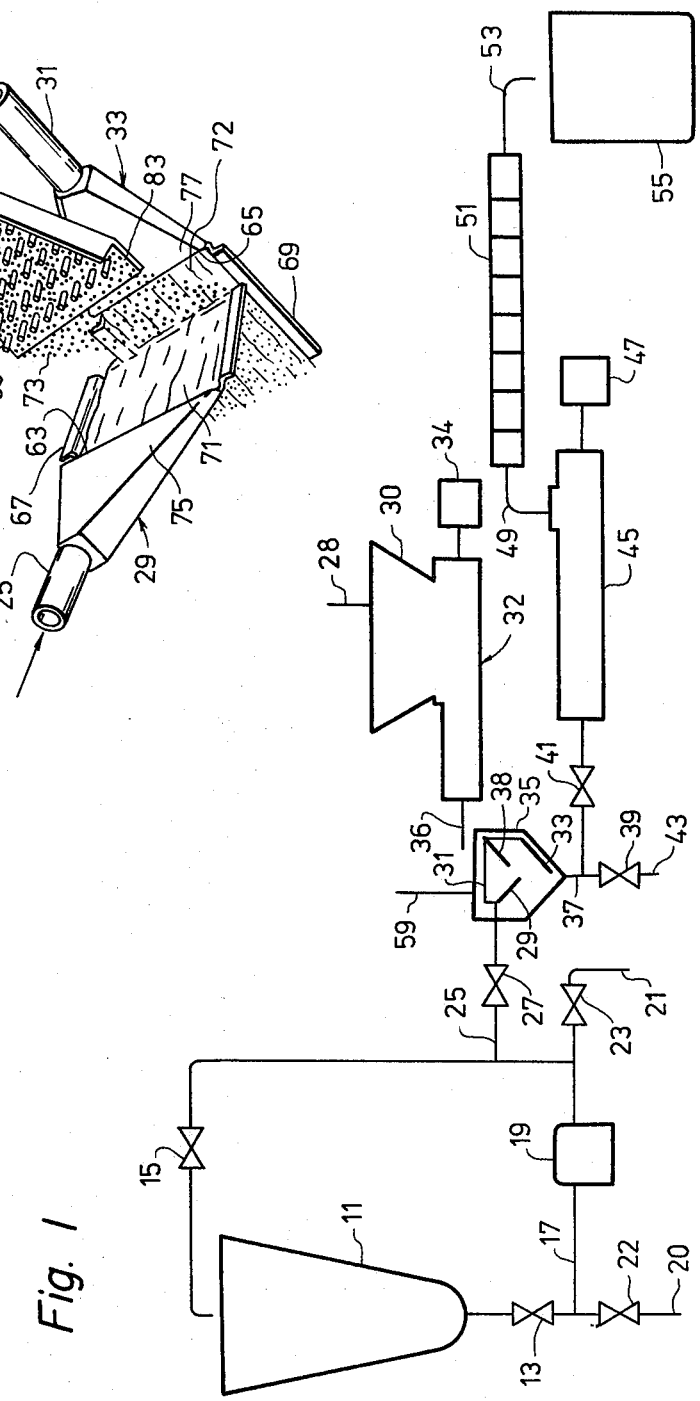

METHOD AND APPARATUS FOR MANUFACTURING DENTIFRICE CONTAINING DISPERSED SPECKLES

This invention relates to manufacturing dentifrices containing speckled materials. More particularly, it relates to making clear gel dentifrices containing evenly distributed and substantially evenly sized functional speckles which also give the dentifrice an attractive appearance.

Dentifrices in paste or gel form which contain dispersed speckles have been described in various patents, among which U.S. Pat. Nos. Re. 29,634; 3,711,604; 3,767,791; 3,803,301; 3,955,942; 4,003,971; and 4,089,943 may be taken as typical. Such products are also described in three U.S. patent applications filed the same day as this application by Barth and Norfleet, Hauschild and Principe, and Gibbons. Such patents and applications are incorporated herein by reference.

In the manufacture of speckled dentifrices it has been conventional to mix the speckles with the dental gel or paste, using conventional equipment, and depending on the shearing actions of the mixers to distribute the speckles evenly throughout the dentifrice. While such technique may be a satisfactory one when the speckles are not frangible, when speckles that may be broken up or solubilized due to shearing actions of the mixer are to be blended with a dentifrice the results may be objectionable. Especially when such speckles include a finely divided functional material, such as a polishing agent, held in unitary aggregated form by a binder designed to be softened on storage, so that the speckles on use are distinct but impalpable, it is important to prvent mixing effects from causing the binder to soften or dissolve prematurely in the dentifrice or in a component thereof, and therefore excessive shearing, such as that resulting from the employment of conventional mixers, is to be avoided. In the past this problem has been solved by running mixers at low speed, thereby lengthening mixing times, and sometimes the permissible shearing forces were insufficient to break up clumps of speckles which may have been formed.

Prior to this invention Edward J. Gibbons, a fellow researcher at Colgate-Palmolive Company, invented methods and apparatuses by which speckles were dropped onto a flowing stream of dental composition and adhered to it to produce a dentifrice in which the speckles had been distributed in desired proportion without excessive agitation or disintegration. My invention represents an improvement over that of Gibbons.

The present invention allows the manufacture of speckled dentifrices to be effected efficiently and quickly without the need for the use of any conventionally shearing mixing apparatus. Also, the speckles do not clump together and neither are they disintegrated, and because the process is a speedy one the product is quickly processed and may be filled into tubes before any appreciable softening or solubilizing of the dentifrice binder occurs. Thus, the preferred clear gel dentifrice, with individually visible, separate functional speckles attractively distributed therein, is obtained without any clouding of it due to breaking up of speckles and distribution of the finely divided functional material, such as polishing agent, throughout the dentifrice. It is also considered that this invention represents an improvement over that of Gibbons, referred to above, because it sandwiches the deposited speckles or other bits of particulate material between two dental composition bodies or ribbons and thereby ensures their immobility with respect to such composition, at least for a period before any further mixing is undertaken.

In accordance with the present invention a method for manufacturing a dentifrice containing dispersed discrete speckles therein will comprise producing a plurality of ribbon shaped streams of a gel or paste dental composition which constitutes a major proportion of a dentifrice, producing a stream of speckles to be distributed throughout the dentifrice, directing said stream of speckles onto a surface of at least one of the streams of gel or paste dental composition and controlling the relative feed rates and the proportions of the gel or paste dental composition and the speckles to be dispersed therein so that when the stream of speckles contacts the stream of gel or paste the speckles are insufficient to cover the ribbon surface presented to the curtain, so that the speckles adhere to the gel or paste ribbon, and bringing together at least two of the plurality of streams of the dental composition so that major surfaces thereof adhere together and sandwich the speckles between them. Also within the invention is an apparatus for carrying out the described process. Such apparatus comprises means for producing a plurality of moving or flowing streams of a dental composition, which is usually a dentifrice except for speckles to be distributed therein, and is of such a nature that the speckles will adhere to it. In such an apparatus such streams or ribbons of dental gel may be produced by forcing the gel through an appropriate orifice so that it is extruded from said orifice in or subsequently converted to a desired shape, preferably a flat ribbon. A stream or curtain of speckles, of particle sizes within the No. 10 to 80 sieve range, U.S. Sieve Series, is directed by elements of the apparatus onto the gel ribbon in such manner as to be distributed evenly over the inner portion, up to 90%, of the surface of the flowing ribbon so as to adhere to said ribbon. Another element of the apparatus directs a different ribbon of gel against the first ribbon to adhere to it, and the sandwich made, with speckles inside, is collected in a walled vessel from which it is continuously removed as more gel containing speckles is added thereto or created therein.

Prior to the filing of this application a search was made in Subclasses 366-150, -151; -152; -153; -154; -155; -156; -157; -158; -159; -160; -177; and -181. No patents were found describing the present invention or making it obvious. The most relevant patents noted are U.S. Pat. Nos. Re. 27,681; 3,740,027; 3,948,491; 4,090,262; and 4,125,208. The reissue patent shows the dropping of a dry chemical from a hopper to a feeder, from which it is fed onto a stream or fan of liquid droplets, whereby each particle of the chemical is evenly wetted, and then enters a mixing solution in which it may be more quickly dissolved. U.S. Pat. No. 3,740,027 describes a particle wetting apparatus in which a dry powder is fed onto a revolving wetted roll from which the wetted particles are discharged into a body of the wetting liquid. U.S. Pat. No. 3,948,491 relates to blending a pigment into a plastic material by feeding it as a granular or powder material in separate charges into a bottom of a hopper through which the plastic material in granular or pellet form is fed. The pigment enters the hopper just before a stirrer, which is located just above the hopper discharge to a feed screw of a plastic molding machine. U.S. Pat. No. 4,090,262 discloses mixing and proportioning apparatus for making multicomponent plastic material mixes, with several metering mechanisms being positively coupled to each other so that the proportions of different components fed into a mixing chamber are kept constant. Finally, U.S. Pat. No. 4,125,208, which relates to supplying granular materials to processing machines, illustrates a charging hopper having a plurality of vacuum connections to it at different levels to withdraw objectionable gases from the material in the hopper so that a product made will be free of bubbles. None of these patents shows the structure of the apparatus of this invention and none shows the concept of the process, which is that dentifrice speckles may be sandwiched between moving flat ribbons of gelatinous or adhesive dentifrice, to which such speckles will adhere, such depositing and the production of a speckled dentifrice being effected readily, and with the speckles being deposited in desired concentration without clumping or disintegration of the speckles and without softening and solubilizing thereof during processing.

The invention will be readily understood from the present specification and the following detailed description of the drawing in which:

FIG. 1 is a schematic representation of an apparatus of this invention for making speckled dentifrice from a dental composition and previously produced speckles; and FIG. 2 is an enlarged perspective view of a portion of the "speckling apparatus" of this invention, illustrating application of speckles to gel streams or ribbons.

In FIG. 1 there are shown gel-making vessel 11, which often preferably will be a Hobart or Dopp mixer, into which the various components of the dental gel, including vehicle, gelling agent, polishing agent, flavor, detergent, colorant, preservative and any other adjuvants, are mixed together, sometimes under vacuum, to form a dentifrice to which speckles, preferably functional speckles, such as those based on a dental polishing agent, are to be added to produce a speckled dentifrice. Valves 13 and 15 in line 17, together with controllable speed positive displacement pump 19, allow recycling of the gel through the mixer, if desired. Lines 20 and 21, and valves 22 and 23 permit discharge of the dental gel (or paste) for cleaning or production of a dentifrice not containing any speckles. Line 25 and valve 27, when opened, with valves 15, 22 and 23 closed and with valve 13 open, gel pump 19 operative and mixing means 11 containing dental gel, allow delivery of the gel at a controlled rate to gel feeding means 29 and through line 31 to a similar but opposing gel feeding means 33, both of which means include relatively restricted and flattened orifices or nozzles, as better illustrated in FIG. 2. They also desirably include additional supporting means for the gel as it leaves the nozzles to help it maintain its ribbon shapes and to guide its flows. Pump 19 may be set to control the gel feed rate so that by controlling the feed rate of the speckles the desired proportion of speckles may be continuously added to the flowing gel. Preferably, pump 19 will be one which subjects the gel to little or no shearing action, so as to maintain its consistency (viscosity). Screw pumps with walls of elastomer are preferred, such as those of the Moyno type. Gel feeding means or extruders 29 and 33 and line 31 are preferably enclosed in a walled vessel or container 35 and usually will be centrally positioned therein so that sandwiches of gel with speckles in the interior thereof, produced in such vessel, will fall vertically or substantially vertically to the bottom thereof near the center of the vessel, from which they may be removed through an outlet communicating with line 37. The outlet (unnumbered) is at the base of the vessel and it is preferable that the gel feeding means 33 terminate near the outlet to diminish rippling of the ribbon sandwich containing speckles which can cause air entrainment (when vacuum is not employed). Also it is preferred that the outlet shape match the ribbon shape (usually flat rectangular) and be oriented with it to minimize obstructions to dentifrice withdrawal from the walled vessel, and so to minimize holdup time, air entrapment, and speckle binder solubilization.

The speckles to be added to the dental gel in prescribed proportion are contained in a hopper 30 of a controllable flow rate feeder 32, preferably of a helix type, including speed control and motor combination 34, which feeder discharges the speckles at a desired controlled rate through an outlet of a tube 36 onto a distributor 38, which spreads them out so that as they leave it they form a falling stream or thin curtain which matches in size and orientation the ribbons produced by nozzles 29 and 33. Instead of a helical feeder, other feeders of the screw, belt and vibratory types are also useful. Line 28 connects to a vacuum source, which, like vacuum line 59 (FIG. 1) may or may not be activated or connected.

Valves 39 and 41 are provided to selectively allow dropping of the product through line 43 or communication with pump 45, which is preferably of the Moyno type. Screw pump 45, powered by motor 47, pumps the product in a gentle manner through line 49 to static mixer 51, preferably of the Kenics type, where it is gently blended without disintegration or solubilization of the speckles therein, and is uniformly mixed. It then passes through line 53 to a receiver 55, which may be feed tank for a tube filling machine, not illustrated.

Although the apparatus of the invention may be used and the process thereof may be practiced without employing vacuum, often it will be desirable to avoid the intrusion of air into the dental materials and the entire operation or any part of it may be under vacuum. Desirably, the speckles feeder and speckles "applicator" will be under vacuum and accordingly, vacuum lines or taps 59 and 28 are indicated in the drawing.

In FIG. 2 gel feeding means 29 and 33 include nozzle portions 75 and 77 having restricted flat openings 63 and 65, respectively, with the nozzle portions, as illustrated, having connected to them supporting guides 67 and 69, respectively, which may be adjustable, and which facilitate proper directings of the ribbons or webs of gel so that the curtain or screen of speckles may fall on them correctly. The gel ribbon on guide 67 is designated by numeral 71 and is shown without speckles having been deposited on it. A similar ribbon 72 on guide 69 discharges its gel ribbon below the discharge from the first guide, and near to the outlet from the vessel. Preferably, the curtain of speckles drops vertically or substantially vertically onto gel ribbon 71 after that ribbon has left the guide 67 but while it is still moving in a direction with a horizontal component, e.g., at 60° from the horizontal. However, if care is exercised some speckles can be dropped onto gel 71 while it is still in contact with the support. As the gel ribbon 71 with adherent speckles falls vertically or substantially vertically it contacts ribbon 72 and the two ribbons sandwich the speckles between them. To avoid rippling, which can cause air entrapment, guide 69 may preferably extend, either straight or as a convex curve, to near (usually within 5 to 25 cm.) of the outlet opening from the vessel and the gel ribbon passes through the oriented and similarly shaped outlet without rippling, with the discharge rate being kept the same as the sum of the addition rates. The rates of feeds (and thicknesses) of the gel ribbons may be about the same or may be varied with such relative rates usually being within the 1:4 to 4:1 range. The controlled and proportioned feed of discrete speckles passes from delivery tube 36 onto distributor 38, which is shown in the form of an expanding shute, including side walls 79 and 81, bottom 83 and dividing pegs 85, located in "Pascal's triangle" arrangement. The speckles and the gel feeding means and the openings in the discharge "nozzle" portions of such gel feeding means may be adjustable. Thus, the gel ribbon feed directions could be changed as desired, and the angle of discharge could be varied but the feed direction should have a horizontal component which is usually from 0° to 45°, e.g., 10° to 30°, from the horizontal, and the feeds are at least partially opposed. Also, the rectangular orifice could be changed in size, so as to be more restricted, but care should be exercised to keep the gel ribbon coherent so that it will not be thin beyond the gel strength. Usually it will be from 1 mm. to 1 cm. thick, e.g., 2 to 6 mm. The first or upper stream or ribbon of gel is directed so that the stream or curtain of speckles, usually 0.5 to 5 mm. thick, may fall on it correctly, preferably when the speckles are falling substantially vertically and the gel is moving in a direction with a horizontal component, so that the gel passes under the falling speckles, which contact it and adhere to it. The gel ribbon 71 is shown falling downwardly and to the right, while speckles 73 fall onto it from distributor 38 of directing means 35 (FIG. 1), and ribbon 72 falls downwardly and to the left below ribbon 71.

In a preferred process of this invention a speckled clear gel dentifrice is made of the formula and by the method described in Example 1 of the U.S. patent application Ser. No. 307,273 filed Sept. 30, 1981 the same day as the present application by Barth and Norfleet. Because the formulations of the dental composition and the speckles are not parts of this invention they will not be detailed herein but it will be noted that the composition is adhesive with respect to the speckles, is preferably a coherent transparent gel and normally the proportion by weight of dentifrice speckles, such as those described in the referred to example, will be in the range 1 to 10%, preferably 2 to 5% of the finished dentifrice. Any of the usual gelling agents for aqueous dentifrices, such as sodium carboxymethyl cellulose (CMC), polyvinyl pyrrolidone, methyl cellulose, carrageenan, will normally make the aqueous dental composition sufficiently tacky in normal gelling concentrations, e.g., 0.2 to 1%. The various gel (or paste) components are mixed together in mixer 11 and are pumped, preferably by a Moyno type pump, to the extruders, which may terminate in flat "slit" nozzles, as illustrated with relatively narrow rectangular openings and longitudinally walled pans or supports. Preferably the nozzles will be inclined downwardly from the horizontal at an angle of about 10° to 45°, e.g., 30°.

The feed rate of the speckle feeding mechanism, which is preferably an Acrisan helix feeder, is adjusted to correspond to the gel feed rate. Thus, when, for example, a 3% speckle content in the dentifrice is desired, if the feed rate of gel is 3 kilograms per minute, then the speckles will be fed at the rate of 93 grams per minute. Conventional electronic or mechanical means may be employed to maintain the desired feeds ratio, or to adjust it if changes in such proportions are desired for different products.

In the drawing the feeding mechanism for the speckles is shown only schematically in FIG. 1 and only the end portion thereof is shown in FIG. 2 but various types of feeds, including screw, belt, weighing belt, electronically controlled gravimetic feeders, and others may be used and the discharge pattern may be changed. The discharge will preferably be such that few, if any, speckles will fall past the gel and the gel stream will hold the impinging speckles. Also, the speckles will fall separately and the gel will be moving fast enough underneath them, at a speed usually of 10 to 100 cm./second, e.g., 20 to 50 cm./sec., that individual speckles strike the gel and adhere to it, with only a few hitting other held speckles and bouncing off them. Also, all or almost all of such bouncing speckles will subsequently adhere to the dental composition ribbon on which they are intended to be deposited or onto the other ribbon.

In the drawing the feeding mechanism for the speckles is shown as a shute with pegs located thereon in a Pascal triangle arrangement. Such shute is downwardly inclined, usually at an angle between 10° and 60° from the horizontal, e.g., at about 30°, and is located so as to deliver a vertically falling curtain which will contact the flowing ribbons or webs of gel but without overlapping them. Thus, the shute will normally be a little narrower, e.g., 10% less, than the supporting means for the gel, or the nozzle exit. Other distributing means than Pascal triangle pegs may also be employed, including, for example, vibratory devices, sometimes combined with screens.

The speckled gel sandwich with the speckles adherent to it, remains for only a short period of time in the walled vessel in which or above which the speckling apparatus is located because it is fed almost directly through the center outlet of such vessel. This short residence time in the "speckling vessel" is highly desirable and helps to maintain the integrity of the speckles in the dentifrice. While residence times in the vessel may vary, typical total times are in the range of 2 seconds to 2 minutes, the shorter the better. Such quick throughput, the absence of mobile speckles and the central gel discharge from the vessel also help to avoid aggregation of speckles into objectionable clumps. The additional volume of the walled vessel is for holding gel which may be fed into it during periods when filling equipment may be temporarily halted and before feed to the vessel can be stopped. Thus, often the walled vessel may contain only a small proportion of speckled gel, e.g., 5 to 25% of its volume.

After leaving the speckling vessel the gel is gently pumped by a Moyno type pump and passes through a static mixer, to assure complete mixing. The preferred static mixer, a Kenics mixer, is like that described in the Mar. 19, 1973 edition of Chemical Engineering in an article entitled *Handling Viscous Materials—Motionless Mixer for Viscous Polymers.* Although it is desirable to utilize a mixer prior to discharging the gel to a filling machine or suitable container before such machine, it is conceivable that the present process and apparatus, without such mixer, could sufficiently distribute the speckles throughout the gel, so that in some instances the mixer would not be employed.

The conditions of operations are not considered to be critical but it is usual that the vacuum employed will be within the range of about 300 to 700 mm. of mercury, e.g., 400 to 600 mm. Hg. Temperatures may be about room temperature or suitably elevated, as from 10° to 40° C. The pressure of extrusion of the gel varies with the gel viscosity but from 0.03 to to 0.7 kilograms per square centimeter appears to be a reasonable range.

The various pieces of equipment of this invention, because they are employed in processing an oral product, should be constructed of non-corroding and safe materials. It has been found that stainless steel components are highly preferable and the mixers, extruders, pumps and valves, and any other parts that contact liquid or gel materials, will preferably be made of stainless steel, such as is normally employed in the food processing industry.

For improved flow properties for gels or pastes a low friction coating or polymeric material such as polytetrafluoroethylene may be employed and such is particularly useful for the gel contacting surfaces of the feeding means, and the vessel, especially the vessel discharge opening.

When a 2% speckled clear dentifrice (containing silicon dioxide, sorbitol, glycerol, CMC, sodium lauryl sulfate, flavor and water in the gel, and alumina and ethyl cellulose in the speckles), like that described in Example 1 of the Barth-Norfleet patent application, previously referred to, is made by the method of this invention, utilizing the apparatus described herein, the product resulting will be just as desired, with the speckles being regularly distributed throughout the clear gel and with no cloudiness or disintegrated speckles noted. Additionally any air entrapment, when vacuum is not utilized, will be minimized. Similar results are obtainable when other speckled dentifrices described in the Barth-Norfleet patent application and the earlier mentioned patents are produced, utilizing the apparatus and process of this invention, as illustrated.

In practicing the inventive process, while it will be preferred for the dental gel or paste to be in flat ribbon form, it is understood that variations of such form may be utilized, such as arced ribbons and even cylindrical or tubular streams. Also, while it is preferred that the stream or curtain of speckles be a suitably thin straight curtain of such material, e.g., 0.1 mm. to 1 cm. or 0.5 to 5 mm., in thickness, falling by gravity, the speckles may be forcefully directed onto the dentifrice.

The proportion of speckles fed to the moving ribbons or webs of gel dental composition will be a minor proportion, compared to the complete dentifrice containing speckles, and compared to the gel fed. (All percentages and proportions mentioned in the specification are by weight, unless otherwise indicated). The feed rate for the speckles will usually be adjusted so that the amount of speckles directed onto the gel will be insufficient to cover it and preferably will be insufficient to cover more than half the area of the portion of the gel exposed to the curtain of speckles when such curtain contacts the gel. While, as was mentioned previously, different ways of adhering the speckles to the gel ribbon have been mentioned, it is highly preferable that the speckles be dropped vertically in a curtain onto the first ribbon of gel, with the gel moving in a direction with a horizontal component. Such direction may be horizontal or have a significant horizontal component with the gel falling after having picked up the speckles, but normally an inclination from the horizontal will be preferred for the gel, with the speckles falling vertically, after having been discharged from a delivery apparatus. The second gel feeder, under the first one, will often be similarly oriented, but at least partially opposing the first feeder.

The viscosity of the gel is not critical, so long as the speckles sufficiently adhere to it, and the sizes of the particles are not critical, but normally they are in the No's. 10 to 80 sieve size range, preferably 30 to 80, and more preferably 30 to 60. The speckles are preferably sharp edged and in falling onto the gel stream they become partially embedded therein, immediately being rendered immobile, but similar good results may also be obtained when rounded speckles are used. Although the speckles used are preferably visible in a clear gel, which makes the product aesthetically attractive, they may be of an index of refraction which renders them invisible. Thus, the designation "speckles" includes visible and invisible discrete particles of various materials, with agglomerates of finely divided polishing agents being preferred. Also, while it is preferred that they be agglomerates of finely divided polishing agent and binder they may comprise other "active" components, such as therapeutic agents, colorants, flavors and fluorides.

It is contemplated that the dentifrice materials on which speckles are deposited and into which they are sandwiched will be all the dentifrice, except speckles, but this is not necessary. It is possible that some dental components may be blended in with the other dentifrice materials after addition of the speckles. For example, it may be desirable to blend in the flavoring, which may contain some volatile components, before the Kenics mixer but after any application of vacuum to the product during sandwiching of the speckles. Such a procedure would have the advantages of preserving the flavor, preventing losses of more voltatile components thereof due to the application of the vacuum in the speckling operation, and any flavor components which would solubilize the binder of the speckles would have less processing time contact with them. Yet, the Kenics or other relatively low shear static mixer would blend the flavoring evenly throughout the dentifrice. Similarly, other components, usually minor adjuvant components, could be added to the dentifrice subsequent to the incorporation of the speckles therein.

The walled vessel mentioned, into which the speckled dentifrice falls, may be under vacuum or may be opened to the atmosphere. The speckling apparatus may have a reservoir underneath it, rather than being enclosed in a vessel. However, it is sometimes preferred that such equipment be covered and under vacuum, when, due to the nature of the materials air entrapment could still be a problem, and it is prefered that it act as a container for the speckling apparatus, in addition to being a vessel to hold the product made. The present process and apparatus lend themselves to use for making a variety of different dentifrice formulas containing different proportions of speckles. To vary the speckles concentration is a simple matter, since it involves only changing the speed of the speckles feeder and controlling the gel feed rates accordingly.

Among the various advantages of the invention are increased efficiency of operation, diminution of employment of moving part mixers, production of gel dentifrices free of air bubbles and with speckles or other discrete functional particles evenly distributed therein, and the stabilization of the dental gel or paste. It is known that various dentifrices are thinned by excessive mechanical working and the present blending operation for adding speckles to the dentifrice avoids such working and allows maintenance of the desired viscosity of the dental gel.

The present invention has been described with respect to various examples and preferred embodiments thereof but is not to be limited to these because it is evident that one of skill in the art, with the present specification before him, would be able to utilize substitutes and equivalents without departing from the invention.

What is claimed is:

1. A method for manufacturing a dentifrice containing dispersed discrete speckles therein which comprises producing a plurality of ribbon shaped streams of a gel or paste dental composition which constitutes a major proportion of a dentifrice, producing a stream of speckles to be distributed throughout the dentifrice, directing said stream of speckles onto a surface of at least one of the streams of gel or paste dental composition and controlling the relative feed rates and the proportions of the gel or paste dental composition and the speckles to be dispersed therein so that when the stream of speckles contacts the stream of gel or paste the speckles are insufficient to cover the ribbon surface presented to the curtain, so that the speckles adhere to the gel or paste ribbon, and bringing together at least two of the plurality of streams of the dental composition so that major surfaces thereof adhere together and sandwich the speckles between them.

2. A method according to claim 1 wherein the streams of gel or paste dental composition are a pair of ribbons of gel continuously flowing in partially opposing directions having horizontal components, and the stream of speckles is directed so as to fall downwardly onto one of the flowing gel ribbons and the amount of speckles in the falling curtain is insufficient to cover more than half of the area of the ribbon surface presented to it.

3. A method according to claim 2 wherein the gel or paste dental composition constitutes all the dentifrice except for the speckles to be distributed therein and is of such a nature that the speckles will adhere to it, the ribbons of such gel are produced by forcing the gel through an opening and converting it to ribbon form, the stream of speckles forms a falling curtain and the speckles are of particle sizes within the No. 10 to 80 sieve range, U.S. Sieve Series, said speckles are directed onto the gel ribbon in such manner as to be distributed evenly over the covered width of the flowing ribbon and adhered to said ribbon before the speckles are sandwiched between the two ribbons, and the combination sandwich of speckles and gel is collected in a walled vessel from which it is continuously removed as more gel containing speckles is added thereto.

4. A method according to claim 3 wherein the ribbons of gel are directed downwardly at an angle of about 30° to 60° from the horizontal, the gel ribbons are supported after being extruded, the gel ribbons fall into the walled vessel at angles with horizontal components and the gel ribbon onto which the speckles are deposited is falling in a path with such a horizontal component when it is contacted by the speckles, and the sandwich falls vertically in the walled vessel to a bottom outlet, from which it is removed.

5. A method according to claim 4 wherein the walled vessel encloses means for converting the gel to ribbon form, the curtains of speckles are produced by widening out a narrow falling stream of speckles to a width slightly less than that of the gel ribbon, the gel ribbon onto which the speckles are falling to be adhered thereto is directed downwardly at an angle about 45° from the horizontal, the second gel ribbon is formed lower than the first gel ribbon and near the vessel bottom, and the speckled gel resulting is withdrawn from the walled vessel by means of an elastomerlined screw pump, mixed in a static mixer and fed to a container, ready for transfer to a tube filling machine.

6. A method according to claim 5 wherein the speckled gel is withdrawn from the vessel through an opening shaped like the speckle-gel sandwich and oriented with such falling sandwich so that the dentifrice exits from the vessel without being distorted to conform to a differently shaped opening.

7. A method according to claim 1, conducted under vacuum.

8. A method according to claim 6 conducted under a vacuum in the range of 300 to 700 mm. of mercury.

9. An apparatus for manufacturing dentifrice containing dispersed speckles therein which comprises means for producing a plurality of streams of gel or paste dental composition, means for producing a stream of speckles to be distributed throughout a dentifrice and for directing said speckle stream onto a surface of a stream of gel or paste dental material, means for controlling relative feed rates and the proportions of the gel or paste dental material and the speckles to be distributed therein, so that when the curtain of speckles contacts the stream of gel or paste the speckles are insufficient to cover the stream surface presented to the curtain and the speckles adhere to the gel or paste of the stream, and means for directing a separate stream of gel so that it adheres to the gel to which the speckles are adhered and sandwiches the speckles between the streams, so that there is produced a gel or paste dentifrice containing speckles in desired proportion distributed in it.

10. An apparatus according to claim 9 wherein the means for producing the streams of dental composition produces a pair of ribbons of gel continuously flowing in directions having horizontal components, the means for producing a stream of speckles and directing them onto the surface of a ribbon of gel directs the speckles to fall downwardly as a curtain onto such flowing gel ribbon and the means for controlling the relative feed rates and proportions of the gel and speckles controls them so that the amount of speckles in the falling curtain is insufficient to cover more than half of the area of the ribbon surface presented to it.

11. An apparatus according to claim 10 wherein the means for producing the gel ribbons includes two extruders, the means for producing the curtain of speckles includes a feeder of the helix, screw, belt or vibratory type and means for distributing the speckles fed thereby into a curtain of width slightly less than the width of the gel ribbon, and which apparatus includes a walled vessel in which the means for extruding the gel ribbons and the means for producing the curtain of speckles are located.

12. An apparatus according to claim 11 wherein the means for producing the gel ribbons communicate with a common source of gel and the means for producing the gel ribbon onto which the speckles are deposited includes supporting and guiding means adjacent the extruder for supporting and guiding the ribbon of gel in a downward path so that it is directed at an angle of about 30° to 60° from the horizontal, the means for producing the curtain of speckles directs such speckles downwardly so that they fall in a substantially vertical curtain onto the gel ribbon, the means for producing the second gel ribbon is located below the means for producing the first gel ribbon, and such second ribbon is directed in a path having a horizontal component and at least partially opposing the path of the first ribbon.

13. An apparatus according to claim 12 wherein the walled vessel has a bottom exit opening, and the ribbon producing means and the means for producing the curtain of speckles are so located that any speckles which may bounce off the first gel ribbon will be deposited on the second gel ribbon and so that the gel-speckles sandwich will exit from the walled exit through the bottom exit opening thereof immediately after production thereof.

14. An apparatus according to claim 13 in which the bottom exit opening in the walled vessel is shaped like the cross-section of the speckle-gel sandwich and is so oriented with the falling sandwich that the dentifrice sandwich may exit from the walled vessel without substantial distortion.

15. An apparatus according to claim 14 including a screw pump and a static mixer, the screw pump being located in communication with an outlet from the walled vessel in which the speckled dentifrice is made so as continuously to withdraw the dentifrice from such vessel and pump it through the static mixer without disintegrating or dissolving speckles thereof in the dentifrice and so that the dentifrice may be delivered to a tube filling machine without objectionable change in the appearance in the speckles.

16. An apparatus according to claim 9, comprising an enclosing walled vessel and vacuum means communicating therewith so as to maintain it under vacuum and thereby prevent air entrapment in the speckled dentifrice.

17. An apparatus according to claim 14 wherein vacuum means communicate with the walled vessel so as to maintain it under vacuum and thereby prevent air entrapment in the speckled dentifrice.

* * * * *